US010147206B2

(12) United States Patent
Li et al.

(10) Patent No.: US 10,147,206 B2
(45) Date of Patent: Dec. 4, 2018

(54) DETERMINING PET SCANNING TIME (71) Applicant: SHENYANG NEUSOFT MEDICAL SYSTEMS CO., LTD., Shenyang (CN)

(72) Inventors: Ming Li, Shenyang (CN); Zhipeng Sun, Shenyang (CN)

(73) Assignee: Shenyang Neusoft Medical Systems Co., Ltd., Shenyang (CN)

( * ) Notice: Subject to any disclaimer, the term of this patent is extended or adjusted under 35 U.S.C. 154(b) by 2 days.

(21) Appl. No.: 15/246,442

(22) Filed: Aug. 24, 2016

(65) Prior Publication Data

US 2017/0084057 A1    Mar. 23, 2017

(30) Foreign Application Priority Data

Sep. 17, 2015   (CN) .......................... 2015 1 0593359

(51) Int. Cl.
*G06K 9/00* (2006.01)
*G06T 11/00* (2006.01)
*A61B 6/03* (2006.01)
*A61B 6/00* (2006.01)
*A61B 6/04* (2006.01)

(52) U.S. Cl.
CPC ............ *G06T 11/003* (2013.01); *A61B 6/032* (2013.01); *A61B 6/037* (2013.01); *A61B 6/5282* (2013.01); *A61B 6/54* (2013.01); *A61B 6/0407* (2013.01); *G06T 2207/10081* (2013.01); *G06T 2207/10104* (2013.01)

(58) Field of Classification Search
CPC ............ G06T 2207/10081; G06T 2207/10104
See application file for complete search history.

(56) References Cited

U.S. PATENT DOCUMENTS

| 6,490,476 | B1 | 12/2002 | Townsend et al. |
| 8,064,472 | B1 | 11/2011 | Wang |
| 2004/0030246 | A1 | 2/2004 | Townsend et al. |
| 2006/0079744 | A1 | 4/2006 | Bonner |
| 2007/0131858 | A1 | 6/2007 | Wollenweber et al. |

(Continued)

FOREIGN PATENT DOCUMENTS

| CN | 102018523 A | 4/2011 |
| CN | 101291624 B | 10/2011 |
| CN | 103800027 A | 5/2014 |

OTHER PUBLICATIONS

Werling, A. et al., "Fast implementation of the single scatter simulation algorithm and its use in iterative image reconstruction of PET data," Physics in Medicine and Biology, vol. 47, No. 16, Aug. 1, 2002, 14 pages.

*Primary Examiner* — Oneal R Mistry
(74) *Attorney, Agent, or Firm* — McCoy Russell LLP (57) ABSTRACT

A method and apparatus for determining PET scanning time are provided. According to an example of the method, a CT image is divided into multiple single-bed CT images according to bed information of bed positions for a PET scan, wherein the CT image is obtained by performing a CT scan on a subject of the PET scan, and a one-to-one corresponding relation exists between the multiple single-bed CT images and all of the beds. A residual true coincidence count ratio is estimated for each of the beds based on corresponding single-bed CT image of the bed, and then a scanning time proportion for each of the beds may be determined based on each of the residual true coincidence count ratios for the beds.

16 Claims, 5 Drawing Sheets

(56) References Cited

U.S. PATENT DOCUMENTS

| | | | |
|---|---|---|---|
| 2008/0144764 A1* | 6/2008 | Nishide | A61B 6/4035 378/5 |
| 2009/0262996 A1 | 10/2009 | Samsonov et al. | |
| 2010/0148047 A1 | 6/2010 | Bendriem et al. | |
| 2014/0148684 A1 | 5/2014 | Foo et al. | |
| 2015/0036789 A1* | 2/2015 | Panin | A61B 6/5235 378/4 |
| 2015/0098640 A1* | 4/2015 | Berker | A61B 6/037 382/131 |
| 2015/0297166 A1* | 10/2015 | Goto | G09B 23/286 378/15 |
| 2016/0128664 A1* | 5/2016 | Manjeshwar | A61B 6/5264 378/20 |
| 2017/0164911 A1* | 6/2017 | Lv | A61B 6/037 |

* cited by examiner

DETERMINING PET SCANNING TIME

CROSS-REFERENCE TO RELATED APPLICATIONS

The present application claims priority to Chinese Patent Application No. 201510593359.9, filed on Sep. 17, 2015, the entire contents of which are hereby incorporated by reference for all purposes.

BACKGROUND

The present disclosure relates to determining Positron Emission Tomography (PET) scanning time.

As a detection technology, PET may be applied to detection of tumors, diagnosis of cerebrovascular diseases, and so on. For example, by injecting a compound (hereinafter referred to as a "tracer") labeled by positron radioisotope into a living organism and measuring a space distribution and a time characteristic of rays emitted from the living organism, an image reflecting metabolism of tissues in the living organism may be obtained by means of reconstruction.

When a PET scan is performed on a subject such as a patient, the scan may be performed according to positions of a PET scanning bed, where different bed positions may correspond to different body regions such as a head or an abdomen of the subject. Images corresponding to multiple bed positions may be merged together to constitute a whole-body scan image of the PET scan. When a whole-body scan is performed on a subject, since structures of regions are different, ratios of attenuation and scattering of rays for scanning bed positions may likely be different. Therefore, in practical use, imbalanced image qualities of different regions may be caused if identical scanning time is utilized for each bed position.

NEUSOFT MEDICAL SYSTEMS CO., LTD. (NMS), founded in 1998 with its world headquarters in China, is a leading supplier of medical equipment, medical IT solutions, and healthcare services. NMS supplies medical equipment with a wide portfolio, including CT, Magnetic Resonance Imaging (Mill), digital X-ray machine, ultrasound, Positron Emission Tomography (PET), Linear Accelerator (LINAC), and biochemistry analyser. Currently, NMS' products are exported to over 60 countries and regions around the globe, serving more than 5,000 renowned customers. NMS's latest successful developments, such as 128 Multi-Slice CT Scanner System, Superconducting MM, LINAC, and PET products, have led China to become a global high-end medical equipment producer.

BRIEF DESCRIPTION OF DRAWINGS

Features of the present disclosure are illustrated by way of example and are not limited to the following figure(s), in which like numerals indicate like elements, and where.

DETAILED DESCRIPTION

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Figure 1A:
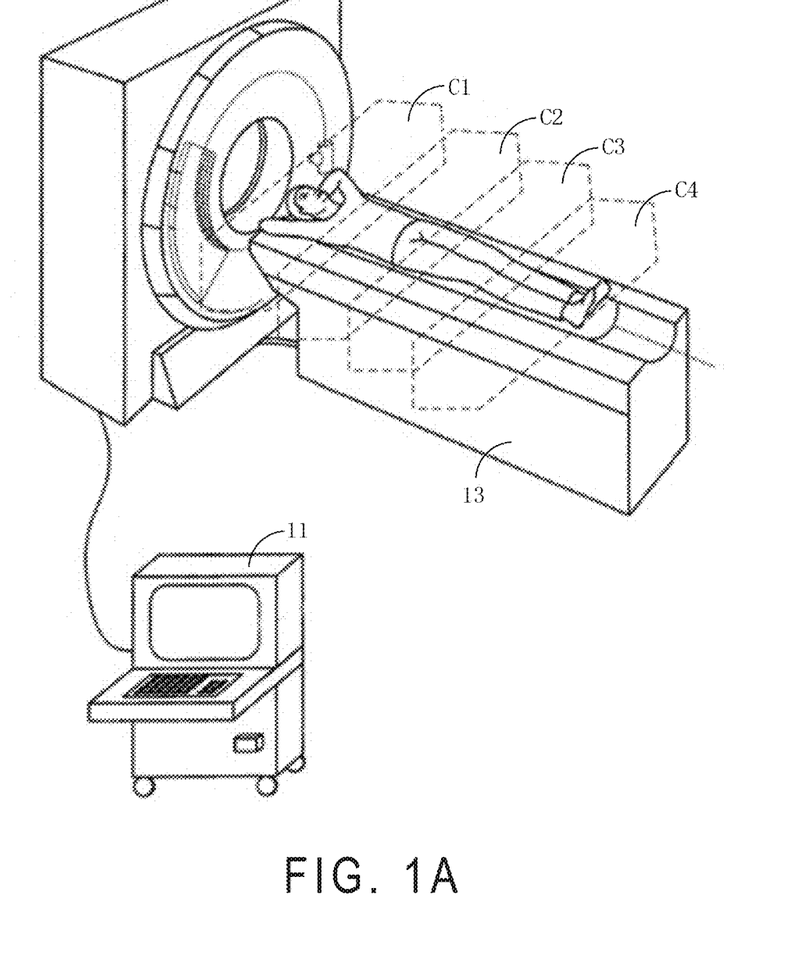
FIG. 1A schematically illustrates a PET scan scene according to an example of the present disclosure.

FIG. 1A is an illustration of a PET scan scene according to an example of the present disclosure. During each PET scan process, a PET detector system may be stationary relative to a subject lying on a scanning bed. Thus, each PET scan may refer to a position of the scanning bed (hereinafter each position of the scanning bed may be referred to as "a bed"). Due to a limited axial extent of the PET detector system, a multi-bed scan is generally necessary when a whole body or a large area of the subject is scanned. For example, 5-8 beds of PET scans may be needed for a whole body scan of a subject, depending on the subject's height and an axial coverage of the PET detector system. In other words, a whole body PET scan of a subject may comprise a plurality of beds. Different beds may correspond to different regions of the subject, and PET images corresponding to multiple beds may be merged to generate a PET scan image.

As shown in FIG. 1A, four scanning beds are illustrated, including: a bed C1, a bed C2, a bed C3 and a bed C4. As discussed above, a quantity of beds may not be limited to four. During a PET scan procedure, the PET scan may be performed in sequence from bed C1 to bed C4. As can be seen from FIG. 1A, these four beds from C1 to C4 may be used for scanning different body regions of a subject. For example, bed C1 may be used for scanning above a neck of the subject, bed C2 may be used for scanning a chest and an abdomen of the subject, and beds C3 and C4 may be used for scanning legs of the subject.

Before a PET scan is performed on a subject, a scanning time may be first determined for each scanning bed. For example, bed C1 may be scanned for two minutes, and bed C2 may be scanned for three minutes, etc. After scanning time for each bed is determined, a PET device may scan according to the determined scanning time(s). Referring to FIG. 1A, setup of scanning time(s) may be completed on a control device 11. The control device 11 may be a computer loaded with control software for the PET device. For example, by displaying a human-machine operation interface of the control software on a display screen of the control device 11, an operator may be allowed to set up parameters for the PET scan, including setting up scanning times for all beds, and then to control the scanning of the PET device.

By utilizing a method for determining PET scanning time according to the present disclosure, a PET scanning time proportion for each of all scanning beds may be first obtained.

According to an example, the PET scanning time proportion for each bed may be as shown in the following Table 1.

TABLE 1

| PET scanning time proportions for scanning beds | | |
|---|---|---|
| Beds | PET scanning time proportion | Scanning time |
| C1 | 1 | 1 min |
| C2 | 2 | 2 min |
| C3 | 3 | 3 min |
| C4 | 4 | 4 min |

Table 1 may be displayed on the display screen of the control device 11 as shown in FIG. 1A. Concrete values "1:2:3:4" of the scanning time proportions for beds is merely exemplary, which may be flexibly set up by the operator according to practical application requirements. In addition, a concrete value of scanning time may also be flexibly set up by the operator according to the scanning time proportion. For example, when the scanning time proportion is "1:2:3:4", scanning time of each bed may be respectively set as "one minute: two minutes: three minutes: four minutes", or may be respectively set as "two minutes: four minutes: six minutes: eight minutes" or the like, as long as the scanning time proportion is met.

When setting up scanning time, the scanning time may be determined according to a desired image quality. For example, when a higher image quality is desired, scanning time may be increased on a basis of meeting the scanning time proportion. However, when a desired image quality is not so high, scanning time may be decreased on the basis of meeting the scanning time proportion. In this way, a flexible method for setting up scanning time may be provided for the operator.

The following will describe in detail how to determine the scanning time proportion for each of PET scanning beds.

For a PET scan, the quality of imaging of different beds shall be uniform as far as possible. For example, a substantially identical signal-to-noise ratio of an image may be provided for tissue regions having a roughly identical activity concentration, so that it may be possible to provide a natural transition of each part of a PET scan image obtained by stitching together images corresponding to different beds. The activity concentration as described refers to activity of a tracer per unit volume of a scanned object. However, when a PET scan is performed on a subject, since structures of body regions of the subject are different, different ratios of attenuation and scattering of rays for different beds may result. Thus, a true coincidence count (namely, PET scan original data) received at each bed may be affected, and imaging effects of beds obtained based on the same scanning time may be different. The so-called true coincidence count refers to a cumulative number of occurrence of true coincidence events. The so-called occurrence of true coincidence events refers to a fact that positrons may be released in a decay process of tracer, back-to-back γ photons may be generated when the positrons annihilate, namely, γ rays (abbreviated as rays in the present disclosure) emitted toward an opposite direction may be generated, and occurrence of true coincidence events may be determined when the γ rays do not change in direction in the subject and are all received by a PET detector system.

Figure 1B:
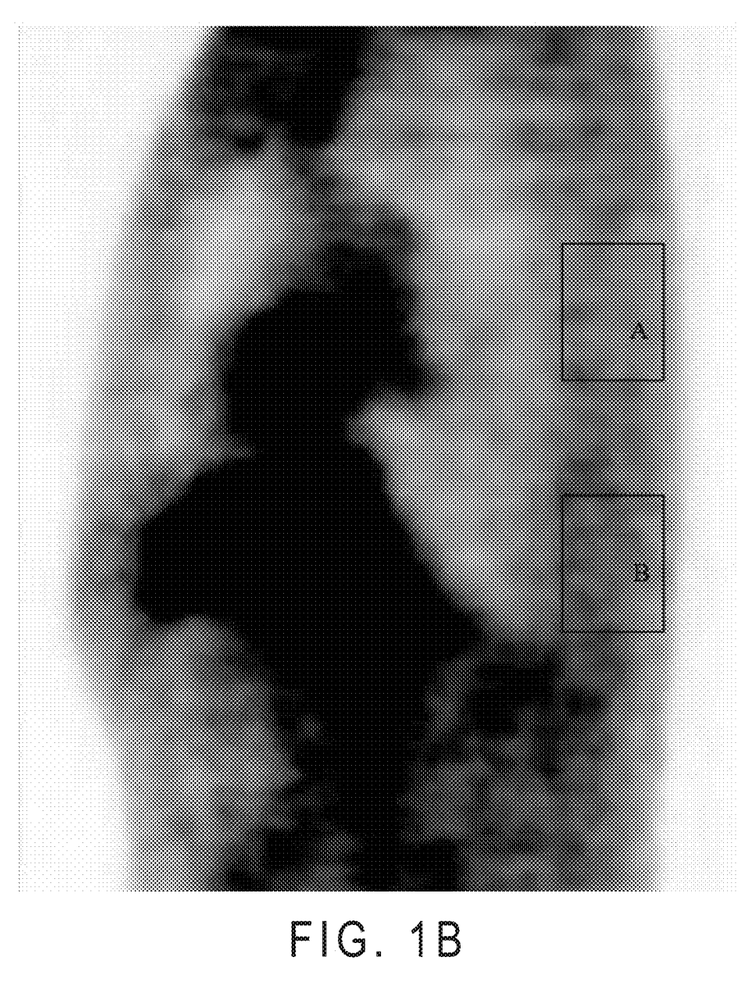
FIG. 1B schematically illustrates an effect of merging together images corresponding to different PET scanning bed positions according to an example of the present disclosure.

For example, as shown in FIG. 1B, Region A and Region B are respectively images obtained by applying the same scanning time for two different beds. As can be seen from the image quality as shown in FIG. 1B, Region B appears inferior to Region A in uniformity. However, actually Region A and Region B correspond to the same tissue structure scope and have identical or similar activity concentration. As can be seen, a PET scan image obtained by merging images corresponding to beds is likely lower in quality when beds corresponding to different tissue regions apply the same scanning time.

In this regard, the inventor realizes that noise estimation may be conducted for a PET image according to a CT (Computed Tomography) image. For example, ratios of attenuation and scattering of true coincidence counts for beds may be estimated and the scanning time proportions for beds may be determined according to the noise estimation so as to equilibrate a true coincidence count actually received at each bed, thereby providing a basically consistent imaging effect for all beds as far as possible.

Figure 2:
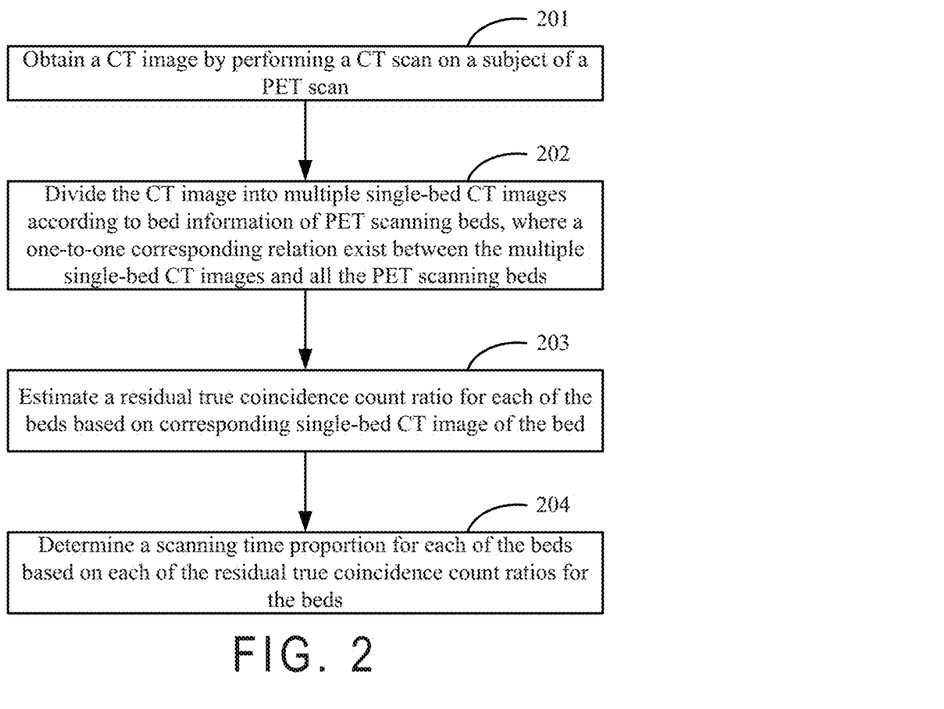
FIG. 2 schematically illustrates a flowchart of a method for determining PET scanning time according to an example of the present disclosure.

FIG. 2 is a flowchart illustrating a method for determining PET scanning time according to an example. As shown in FIG. 2, the method may include following blocks 201-204.

At block 201, a CT image may be obtained by performing a CT scan on a subject of a PET scan.

Before a PET scan is performed on a subject, a CT image may be obtained by performing a CT scan on the subject. For example, a CT pilot scan or a CT scout scan may be performed first to determine a scanning range of the subject, and then a CT axial scan or a CT tomo scan may be performed to obtain a CT image of the whole body of the subject. Generally, a scanning range of a subject may be determined according to a lateral or frontal scout image of the subject obtained by means of a CT scout scan, and a tomographic image of a subject may be obtained by means of a CT axial spiral scan.

After a CT image is obtained, the CT image may be divided at block 202.

According to an example, a CT image may be divided into multiple single-bed CT images according to bed information, where a one-to-one corresponding relation between the multiple single-bed CT images and all the PET scanning beds may be provided. With reference to FIG. 1A, since four beds are included in the PET scan in FIG. 1A, correspondingly, the CT image may be divided into four parts, where each part may be referred to as a "single-bed CT image". For example, one single-bed CT image may correspond to bed C1, another single-bed CT image may correspond to bed C2, and so forth.

In implementation, before a PET scan is performed on a subject, the control device 11 may be used to input relevant information before the PET scan. Exemplarily, a "PET scanning time setup" option may be displayed on a display interface of the control device 11. When an operator clicks the option, the control device 11 may initiate blocks of the method in this example, including: indicating a scanning device 13 to perform a CT scan on a subject so as to obtain a CT image, for example. The scanning device 13 may be a PET/CT integrated device, in some examples. The CT image obtained by performing the CT scan with the scanning device 13 may be transmitted to the control device 11 for further processing. For example, further processing may include division of the CT image at block 202, and may further include subsequent blocks 203 and 204, until the scanning time proportion for each bed is calculated out and displayed on the display interface of the control device 11 so that the operator may set up PET scanning time thereby.

A CT image obtained by a CT scan may be, for example, stored in a memory of the control device 11. The memory of the control device may also store bed information corresponding to PET scanning beds. For example, the bed information may include, referring to FIG. 1A, that bed C1 corresponds to a first position segment of the scanning device 13, and bed C2 corresponds to a second position segment, etc. A CT image may be divided according to bed information. For example, a CT image corresponding to a first position segment may be a single-bed CT image of bed C1, and a CT image corresponding to a second position segment may be a single-bed CT image of bed C2, etc.

At block 203, based on each of the single-bed CT images, a residual true coincidence count ratio for a bed corresponding to the single-bed CT image may be estimated.

Scattering and attenuation of rays may occur when the rays penetrate through the subject, which may lead to decrease of a true coincidence count, and a remaining part may be referred to as a residual true coincidence count. Different beds may correspond to different regions of a subject, and tissues of different regions may likely have different attenuation ratios and scattering degrees of rays. Therefore, at this block 203, based on each of the single-bed CT image, an attenuation ratio and a scattering degree of rays for a bed corresponding to the single-bed CT image may be estimated.

Supposing neither attenuation nor scattering exists, a true coincidence count corresponding to each of four beds may be J. However, in view of attenuation and scattering of rays caused by a tissue structure, a true coincidence count actually received at each bed may be different. For example, a true coincidence count received at bed C1 may be s1, and a true coincidence count received at bed C2 may be s2, etc. Therefore, an attenuation ratio and a scattering degree of rays caused by a tissue region corresponding to each bed may be reflected by determining a residual true coincidence count ratio corresponding to each bed.

In practical implementation, a residual true coincidence count ratio corresponding to each bed may be determined one by one. For example, after single-bed CT images respectively corresponding to beds C1-C4 are obtained by dividing, the single-bed CT image corresponding to bed C1 may be determined first to obtain a residual true coincidence count ratio corresponding to bed C1, then the single-bed CT image corresponding to bed C2 may be determined, and so on until residual true coincidence count ratios corresponding to all beds are calculated out.

After residual true coincidence count ratios corresponding to all the beds are obtained by determination based on each single-bed CT image, at block 204, the scanning time proportion for each bed may be determined.

Still taking four beds as depicted in FIG. 1A as an example, and supposing residual true coincidence count ratios corresponding to beds C1-C4 respectively are $\lambda 1$, $\lambda 2$, $\lambda 3$ and $\lambda 4$, the scanning time proportions for the four beds may be $1/\lambda 1:1/\lambda 2:1/\lambda 3:1/\lambda 4$.

In some examples, determining the scanning time proportion for each of the beds based on each of the residual true coincidence count ratios for the beds may comprise calculating a reciprocal for each of the residual true coincidence count ratios, and setting the scanning time proportion for each of the beds to be equal to the reciprocal of corresponding residual true coincidence count ratio of the bed.

In the method for determining PET scanning time of the present disclosure, a residual true coincidence count ratio corresponding to each bed may be determined and a scanning time proportion for each bed may thus be determined hereby, so that a true coincidence count received at each bed may be roughly identical and an imaging effect corresponding to each bed may be basically consistent. Therefore, it may be possible to provide a natural transition of each part of a PET scan image obtained by stitching images corresponding to beds. Also the method may determine a suitable scanning time proportion according to a body structure of each subject and may ensure a PET scan of a subject to better conform to an actual physical condition of the subject, thereby providing a higher quality of a PET scan image for the subject. In addition, the scanning time proportion for each bed may be determined by using the method depicted herein, which may reduce total PET scanning time as far as possible on the basis of meeting the proportion. Thus, it may be possible to better equilibrate a PET scan efficiency and a PET scan image quality.

With regard to block 203 in FIG. 2, when a residual true coincidence count ratio corresponding to each bed is estimated respectively based on each single-bed CT image, such a determination may be performed based on three kinds of data, namely initial PET data, an attenuation correction factor and a scattering correction factor. The following respectively describes possible methods for acquiring these three kinds of data.

When rays penetrate through a subject, the rays may be blocked with a certain probability, namely the rays may be attenuated, which may cause decrease of a true coincidence count. The attenuation correction factor may denote a correction coefficient for correcting a residual true coincidence count to be a count level without attenuation. According to one example, each of CT values of a single-bed CT image may be converted to a linear attenuation coefficient at energy of 511 keV to obtain a linear attenuation coefficient image, and the attenuation correction factor may be obtained by means of orthographic projection of the linear attenuation coefficient image. The linear attenuation coefficient may be converted to a format the same as that of PET data by means of orthographic projection of the linear attenuation coefficient image. The attenuation correction factor may be denoted by A.

The initial PET data may denote PET data into which neither attenuation effect nor scattering effect may be added. According to one example, the initial PET data may be obtained according to following manner: a binarization process may be performed on a single-bed CT image, for example, the single-bed CT image may be divided into an air part and a non-air part, and image data subjected to the binarization process may be taken as the initial PET data. CT values of air are generally −1000. However, in view of an inherent system error present in a CT scan, CT values of air may fluctuate, for example, the CT values may be smaller by ∼5% than a normal value. Therefore, a part whose CT values are smaller than −950 may be set as the air part. Generally, the air part is not involved with drug absorption, and it may be supposed that the other part denotes tissues having the same drug uptake capacity, namely, other non-air part has the same activity concentration distribution. A single-bed CT image subjected to the binarization process may be taken as an initial PET image into which neither scattering effect nor attenuation effect is added, and image data of the initial PET image may be the initial PET data. The initial PET data may be denoted by E.

Figure 3:
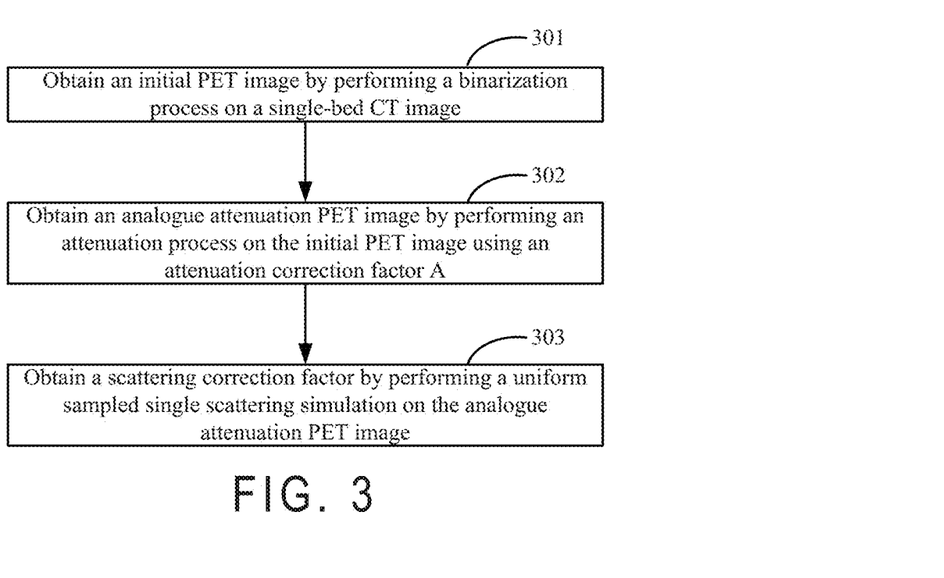
FIG. 3 schematically illustrates a flowchart of a method for acquiring a scattering correction factor according to an example of the present disclosure.

When rays penetrate through a subject, there may be a certain probability of occurrence of scattering, which may change direction, thereby having a negative effect on a true coincidence count. The scattering correction factor may denote a correction coefficient for correcting a residual true coincidence count to be a count level without scattering. According to one example, the scattering correction factor may be obtained according to the flow as shown in FIG. 3. As shown in FIG. 3, at block 301, an initial PET image may be obtained by performing a binarization process on a single-bed CT image, and manners for the binarization process may be obtained by referring to the foregoing initial PET data. At block 302, an analogue attenuation PET image may be obtained by performing an attenuation process on the initial PET image with the attenuation correction factor A. At block 303, the scattering correction factor may be obtained by performing a uniform sampled single scattering simulation on the analogue attenuation PET image. Generally, a relatively accurate scattering correction factor may be obtained by means of a uniform sampled single scattering simulation. This is because the initial PET image generally may be uniformly distributed. The scattering correction factor may be denoted by S.

According to another example, since the initial PET image obtained by performing a binarization process on the single-bed CT image generally may be uniformly distributed, it may be supposed that a subject corresponding to the initial PET images is a cylindrical object, and the initial PET data E may be data on the cylindrical object. A diameter of the cylindrical object may be obtained by performing a scout scan on the subject and by determining according to a total attenuation coefficient in a pilot image obtained by means of the scout scan. Then, a set of scattering ratio parameters may be obtained by measuring phantom bodies of water phantom having different diameters, and the scattering correction factor S may be obtained according to interpolation or fitting of the diameter of the foregoing cylindrical object.

Other methods such as a convolution method may be employed to determine the scattering correction factor S. The so-called convolution method refers to convoluting data by applying a kernel function (convolution kernel). In the present disclosure, the kernel function may be referred to as a scattering kernel which may be calculated out by a PET scan of a water phantom.

After the foregoing initial PET data E, the attenuation correction factor A and the scattering correction factor S are obtained, a residual true coincidence count T may be calculated according to a following formula:

$$(E-S)/A=T.$$

Further, a residual true coincidence count ratio $\lambda$ may be calculated based on the initial PET data E and the residual true coincidence count T according to a following formula:

$$\lambda=T/E.$$

Thus, in some examples, determining the residual true coincidence count ratio for each of the beds according to the initial PET data, the attenuation correction factor, and the scattering factor for the bed may comprise determining the residual true coincidence count ratio for each of the beds by performing a calculation with the following formula:

$$\lambda=(E-S)/(A*E).$$

In the present disclosure, scanning time corresponding to each bed may be set up to improve the quality of a PET scan image obtained by merging images corresponding to beds. Therefore, image quality may be taken into account as one of bases for setting up scanning time. Specifically, in the above-mentioned examples, scanning time proportion $1/\lambda$ may be obtained according to the residual true coincidence count ratio, whereas different residual true coincidence counts may lead to different image qualities. The true coincidence count may be obtained according to parameters such as the scattering correction factor S and the attenuation correction factor A, etc.

Further, when scanning time proportions for four beds are determined, other influence factors may be taken into account. For example, when rays penetrate through a subject, if a direction of rays is changed due to occurrence of scattering, not only the true coincidence count will be reduced, but also it is possible to affect correct estimation of positions where positrons actually annihilate. For example, indeterminacy of positions where positrons annihilate may be created, which may have a negative effect on image quality. Therefore, a scattering impact factor may be determined according to the following formula, which may denote a rough ratio between influence of scattering corresponding to each bed on a true coincidence count and influence on estimation of positions where positrons annihilate:

$$kn=S/(E-S).$$

Wherein the S denotes a scattering correction factor obtained by estimating according to a single-bed CT image corresponding to bed C1; the E denotes initial PET data without attenuation or scattering; the kn is the scattering impact factor, which may denote a rough ratio between influence of scattering of tissues of a subject corresponding to the bed C1 on a true coincidence count and influence on estimation of positions where positrons annihilate.

Influences of the foregoing "residual true coincidence count" and the "scattering impact factor" on image quality may be different. Taking bed C1 and bed C2 as an example, residual true coincidence counts of the two beds may be obtained according to the scattering correction factor S and the attenuation correction factor A of the beds. Image qualities of the two beds may likely be different when the scattering impact factors kn of the two beds are different (for example, kn of bed C1 may be higher, which may denote scattering of tissues of a subject corresponding to bed C1 has greater influence on a true coincidence count; and kn of the bed C2 may be lower, which may denote scattering of tissues of the subject corresponding to the bed C2 has greater influence on estimation of positions where positrons annihilate), even though the identical residual true coincidence counts are obtained for the two beds.

For example, the scattering impact factor of a bed may be further taken into account on the basis of adjusting the scanning time proportion for each of beds according to the residual true coincidence count ratio.

For example, calculating the scanning time proportion for each of the beds may be carried out with a following formula:

$$\tau=1/\lambda+\alpha*S/(E-S),$$

wherein, the E denotes the initial PET data of one of the beds,
the S denotes the scattering correction factor of the bed,
the $\alpha$ denotes an empirical constant,
the $\lambda$ denotes the residual true coincidence count ratio of the bed, and
the $\tau$ denotes the scanning time proportion of the bed.

Exemplarily, with regard to determined scanning time proportions "$1/\lambda 1:1/\lambda 2:1/\lambda 3:1/\lambda 4$" for four beds, the scanning time proportion corresponding to the bed C1 may be $1/\lambda 1$. Supposing the scattering impact factor of the bed C1 is kn, the scanning time proportion corresponding to the bed C1 may be changed from $1/\lambda 1$ to $1/\lambda 1+\alpha*kn$, where a denotes an empirical coefficient which may be an empirical value obtained by experiment.

Figure 4:
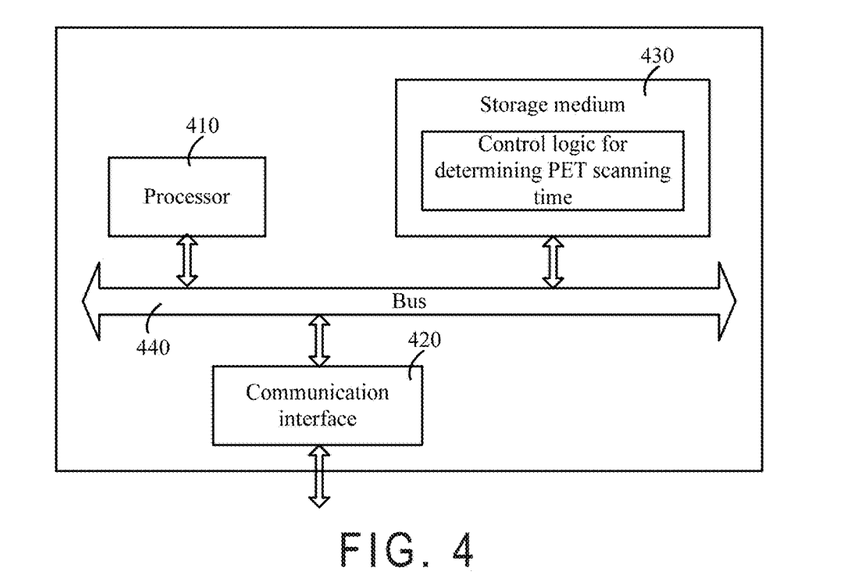
FIG. 4 schematically illustrates a hardware structure of an apparatus for determining PET scanning time according to an example of the present disclosure.

The foregoing method for determining PET scanning time may be executed by the control device 11 as shown in FIG. 1A. The example as shown in FIG. 4 may be referred to for the hardware structure of the control device 11. As shown in FIG. 4, the control device 11 may include: a processor 410, a communication interface 420, a storage medium 430 and a bus 440. Communications among the processor 410, the communication interface 420 and the storage medium 430 may be achieved by means of the bus 440.

The storage medium 430 may store machine-executable instructions corresponding to a control logic for determining PET scanning time. The storage medium may be, for example, a non-volatile memory. The processor 410 may invoke and execute the machine-executable instructions corresponding to the control logic for determining PET scanning time stored in the storage medium 430, to execute the foregoing method for determining PET scanning time. For example, the machine-executable instructions corresponding to the control logic for determining PET scanning time may be control software installed in the control device 11 as shown in FIG. 1A. When the processor 410 executes the machine-executable instructions, the control device 11 may correspondingly display, on a display interface, a function interface corresponding to the machine-executable instructions.

The functions of the machine-executable instructions corresponding to the control logic for determining PET scanning time may be stored in a computer-readable storage medium if these functions are implemented in the form of software function units and are sold or used as independent products. Based on such an understanding, the technical solution of the present disclosure may be embodied in the form of software products, which may be stored in a storage medium and comprise some instructions to cause a computer device (a personal computer, a server or a network device and so on) to execute all or a part of blocks of the method as recited in the examples of the present disclosure. The aforementioned storage medium includes: a USB flash disk, a mobile hard disk, a read-only memory (ROM), a random access memory (RAM), a magnetic disk or an optical disk and other medium capable of storing program codes.

Figure 5:
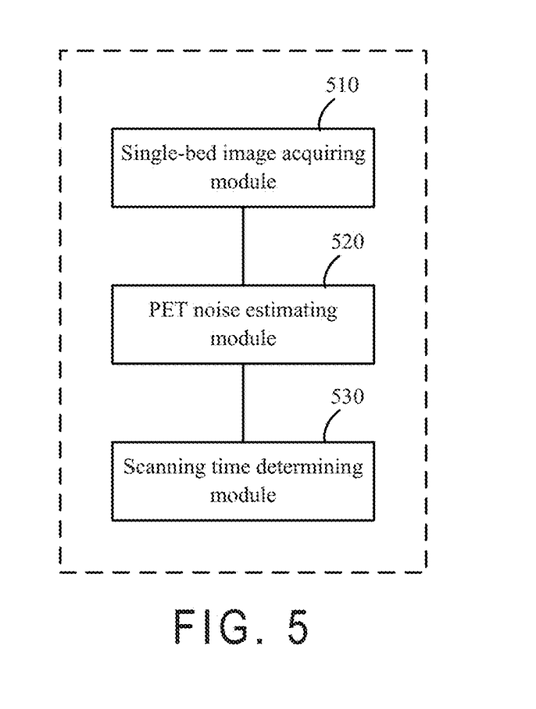
FIG. 5 schematically illustrates a functional module of a control logic for determining PET scanning time according to an example of the present disclosure.

The foregoing machine-executable instructions corresponding to the control logic for controlling PET scanning time may be referred to as an "apparatus for determining PET scanning time", and the apparatus may be divided into various functional modules. As shown in FIG. 5, the apparatus may include a single-bed image acquiring module 510, a PET noise estimating module 520 and a scanning time determining module 530.

The single-bed image acquiring module 510 may be configured to divide a CT image into multiple single-bed CT images according to bed information of PET scanning beds. The CT image may be obtained by performing a CT scan on a subject of the PET scan and dividing the CT scan into multiple single-bed CT images where there exists one-to-one corresponding relations between the multiple single-bed CT images and all the PET scanning beds.

The PET noise estimating module 520 may be configured to estimate a residual true coincidence count ratio for each of the beds based on corresponding single-bed CT image of the bed.

The scanning time determining module 530 may be configured to determine a scanning time proportion for each of the beds based on each of the residual true coincidence count ratios for the beds.

Figure 6:
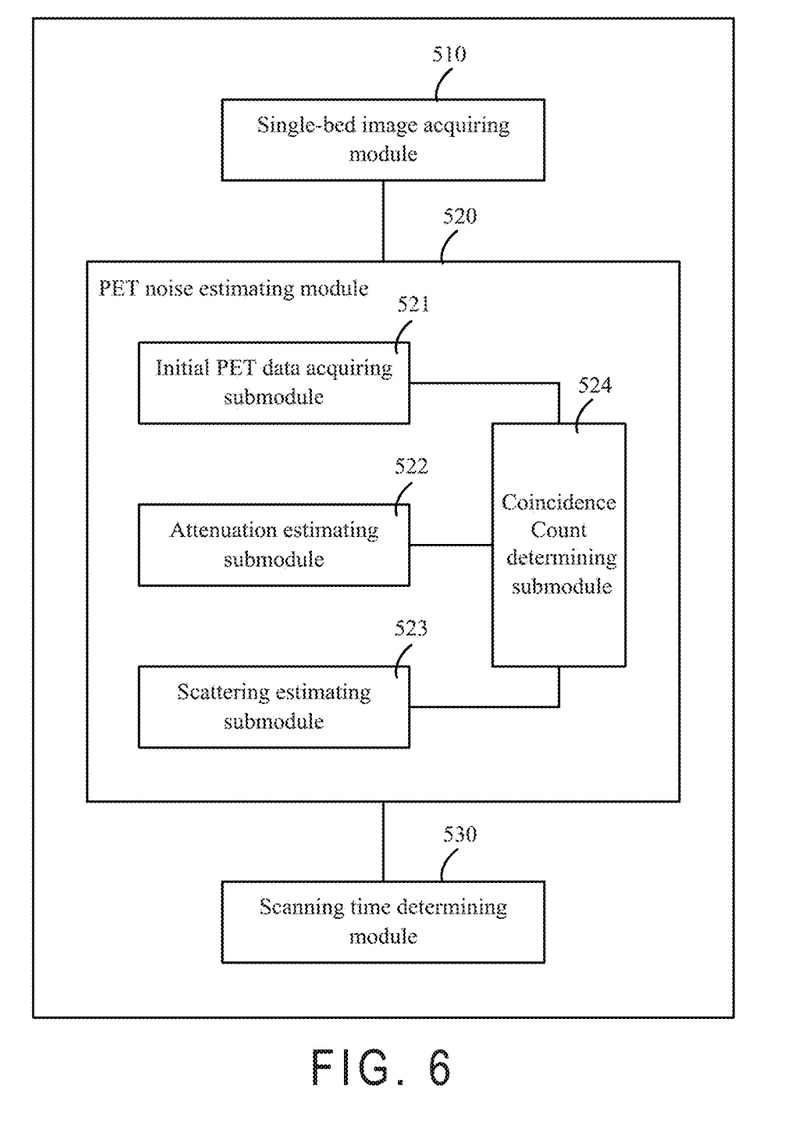
FIG. 6 schematically illustrates another functional module of a control logic for determining PET scanning time according to an example of the present disclosure.

According to another example, as shown in FIG. 6, the PET noise estimating module 520 may further include: an initial PET data acquiring submodule 521, an attenuation estimating submodule 522, a scattering estimating submodule 523 and a coincidence count determining submodule 524.

The initial PET data acquiring submodule 521 may be configured to acquire initial PET data according to a single-bed CT image. The initial PET data may denote original PET data into which neither attenuation effect nor scattering effect may be added.

The attenuation estimating submodule 522 may be configured to obtain an attenuation correction factor according to a single-bed CT image. The attenuation correction factor may denote a correction coefficient for correcting a residual true coincidence count to be a count level without attenuation.

The scattering estimating submodule 523 may be configured to obtain a scattering correction factor according to a single-bed CT image. The scattering correction factor may denote a correction coefficient required for correcting a residual true coincidence count to be a count level without scattering.

The coincidence count determining submodule 524 may be configured to determine the residual true coincidence count ratio of the initial PET data, according to the initial PET data, the attenuation correction factor and the scattering correction factor.

Further, the scattering estimating submodule 523 may be specifically configured to obtain an initial PET image by performing a binarization process on the single-bed CT image, to obtain an analogue attenuation PET image by performing an attenuation process on the initial PET image using the attenuation correction factor, and to obtain the scattering correction factor by performing a uniform sampled single scattering simulation on the analogue attenuation PET image.

Further, when the binarization process is performed on the single-bed CT image, the scattering estimating submodule 523 may divide the single-bed CT image into an air part and a non-air part, and may comprise supposing that all kinds of tissue corresponding to the non-air part have the same activity concentration distribution.

Further, the scanning time determining module 530 may be further configured to adjust a scanning time proportion corresponding to each of the beds by using a scattering impact factor of each of the beds, on the basis of determining a scanning time proportion for each of the beds according to a residual true coincidence count ratio corresponding to the bed.

The above are only preferred examples of the present disclosure and are not intended to limit the disclosure in any way. Within the spirit and principles of the present disclosure, any changes made, equivalent replacement, or improvement in the protection of the present disclosure should be understood to be contained within the range of the present disclosure.

The methods, processes, and units described herein may be implemented by hardware (including hardware logic circuitry), software or firmware or a combination thereof. The term 'processor' is to be interpreted broadly to include a processing unit, ASIC, logic unit, or programmable gate array etc. The processes, methods, and functional units may all be performed by the one or more processors; reference in this disclosure or the claims to a 'processor' should thus be interpreted to mean 'one or more processors'.

Further, the processes, methods, and functional units described in this disclosure may be implemented in the form of a computer software product. The computer software product may be stored in a storage medium and may comprise a plurality of instructions for making a processor to implement the methods recited in the examples of the present disclosure.

The figures are only illustrations of an example, wherein the units or procedure(s) shown in the figures are not necessarily essential for implementing the present disclosure. Those skilled in the art will understand that the units in the device in the example can be arranged in the device in the examples as described, or can be alternatively located in one or more devices different from that in the examples. The units in the examples described can be combined into one module or further divided into a plurality of sub-units.

Although the flowcharts described show a specific order of execution, the order of execution may differ from that which is depicted. For example, the order of execution of two or more blocks may be changed relative to the order shown. Also, two or more blocks shown in succession may be executed concurrently or with partial concurrence. All such variations are within the scope of the present disclosure.

Throughout the present disclosure, the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for determining PET scanning time, comprising:
    performing a CT scan with a CT device to obtain a CT image of a subject;
    dividing the CT image into multiple single-bed CT images according to bed information corresponding to different positional segments of multiple beds of a PET scan, wherein each of the multiple single-bed CT images corresponds to the bed information of one of the multiple beds of the PET scan;
    obtaining initial PET data, an attenuation correction factor, and a scattering correction factor for each of the multiple beds of the PET scan based on the corresponding single-bed CT image of the bed, wherein obtaining the scattering correction factor for each of the multiple beds of the PET scan based on the corresponding single-bed CT image of the bed comprises:
    obtaining an initial PET image by performing a binarization process on the corresponding single-bed CT image;
    obtaining an analogue attenuation PET image by performing an attenuation process on the initial PET image with the attenuation correction factor; and
    obtaining the scattering correction factor by performing a uniform sampled single scattering simulation on the analogue attenuation PET image;
    determining a residual true coincidence count ratio for each of the multiple beds of the PET scan according to the initial PET data, the attenuation correction factor, and the scattering correction factor for the bed;
    determining a scanning time proportion for each of the multiple beds of the PET scan based on the residual true coincidence count ratio for each of the multiple beds of the PET scan;
    setting up respective scanning times for the multiple beds of the PET scan based on the scanning time proportion; and
    performing the PET scan with a PET device in accordance with the respective scanning times for the multiple beds of the PET scan.

2. The method according to claim 1, wherein said obtaining the initial PET data for each of the multiple beds of the PET scan based on the corresponding single-bed CT image of the bed comprises:
    obtaining the initial PET image by performing the binarization process on the corresponding single-bed CT image; and
    taking image data of the initial PET image as the initial PET data.

3. The method according to claim 1, wherein said obtaining the attenuation correction factor for each of the multiple beds of the PET scan based on the corresponding single-bed CT image of the bed comprises:
    obtaining a linear attenuation coefficient image by converting each CT value of the corresponding single-bed CT image into a linear attenuation coefficient at a particular energy; and
    obtaining the attenuation correction factor by means of orthographic projection of the linear attenuation coefficient image.

4. The method according to claim 1, wherein said obtaining the initial PET image by performing the binarization process on the corresponding single-bed CT image comprises:
    dividing the corresponding single-bed CT image into an air part and a non-air part, and
    performing the binarization process on the corresponding single-bed CT image in a condition that all kinds of tissue corresponding to the non-air part have a same activity concentration distribution.

5. The method according to claim 1, wherein said determining the residual true coincidence count ratio for each of the multiple beds of the PET scan according to the initial PET data, the attenuation correction factor, and the scattering correction factor for the bed comprises:
    determining the residual true coincidence count ratio for each of the multiple beds of the PET scan by performing a calculation with the following formula:

$$\lambda=(E-S)/(A*E),$$

wherein E denotes the initial PET data of one of the multiple beds of the PET scan,
    S denotes the scattering correction factor of the bed,
    A denotes the attenuation correction factor of the bed, and
    $\lambda$ denotes the residual true coincidence count ratio of the bed.

6. The method according to claim 1, wherein said determining the scanning time proportion for each of the multiple beds of the PET scan based on the residual true coincidence count ratio for each of the multiple beds of the PET scan comprises:

calculating a reciprocal for the residual true coincidence count ratio; and setting the scanning time proportion for each of the multiple beds of the PET scan to be equal to the reciprocal of the corresponding residual true coincidence count ratio of the bed.

7. The method according to claim 1, further comprising:
determining a scattering impact factor for each of the multiple beds of the PET scan according to the initial PET data and the scattering correction factor of the bed; and adjusting the scanning time proportion for each of the multiple beds of the PET scan with the scattering impact factor of each of the multiple beds of the PET scan.

8. The method according to claim 7, wherein said adjusting the scanning time proportion for each of the multiple beds of the PET scan with the scattering impact factor of each of the multiple beds comprises:
calculating the scanning time proportion for each of the multiple beds of the PET scan with the following formula:

$$\tau=1/\lambda+\alpha*S/(E-S),$$

wherein E denotes the initial PET data of one of the multiple beds of the PET scan, S denotes the scattering correction factor of the bed, α denotes an empirical constant, λ denotes the residual true coincidence count ratio of the bed, and the τ denotes the scanning time proportion of the bed.

9. An apparatus for determining PET scanning time, comprising a processor configured to read and execute machine-executable instructions which correspond to a control logic for determining the PET scanning time and are stored in a machine-readable storage medium, wherein the machine-executable instructions cause the processor to:

perform a CT scan with a CT device to obtain a CT image of a subject;

divide the CT image into multiple single-bed CT images according to bed information corresponding to different positional segments of multiple beds of a PET scan, wherein each of the multiple single-bed CT images corresponds to bed information of one of the multiple beds of the PET scan;

obtain initial PET data, an attenuation correction factor, and a scattering correction factor for each of the multiple beds of the PET scan based on the corresponding single-bed CT image of the bed, wherein when obtaining the scattering correction factor for each of the multiple beds of the PET scan based on the corresponding single-bed CT image of the bed, the machine-executable instructions cause the processor to:

obtain an initial PET image by performing a binarization process on the corresponding single-bed CT image;

obtain an analogue attenuation PET image by performing an attenuation process on the initial PET image with the attenuation correction factor; and obtain the scattering correction factor by performing a uniform sampled single scattering simulation on the analogue attenuation PET image;

determine a residual true coincidence count ratio for each of the multiple beds of the PET scan according to the initial PET data, the attenuation correction factor, and the scattering correction factor for the bed;

determine a scanning time proportion for each of the multiple beds of the PET scan based on the residual true coincidence count ratio for each of the multiple beds of the PET scan;

set up respective scanning times for the multiple beds of the PET scan based on the scanning time proportion; and perform the PET scan with a PET device in accordance with the respective scanning times for the multiple beds of the PET scan.

10. The apparatus according to claim 9, wherein, when obtaining the initial PET data for each of the multiple beds of the PET scan based on the corresponding single-bed CT image of the bed, the machine-executable instructions cause the processor to:

obtain the initial PET image by performing the binarization process on the corresponding single-bed CT image; and take image data of the initial PET image as the initial PET data.

11. The apparatus according to claim 9, wherein when obtaining the attenuation correction factor for each of the multiple beds of the PET scan based on the corresponding single-bed CT image of the bed, the machine-executable instructions cause the processor to:

obtain a linear attenuation coefficient image by converting each CT value of the corresponding single-bed CT image into a linear attenuation coefficient at a particular energy; and obtain the attenuation correction factor by means of orthographic projection of the linear attenuation coefficient image.

12. The apparatus according to claim 9, wherein, when obtaining the initial PET image by performing the binarization process on the corresponding single-bed CT image, the machine-executable instructions cause the processor to:

divide the corresponding single-bed CT image into an air part and a non-air part, and perform the binarization process on the corresponding single-bed CT image in a condition that all kinds of tissue corresponding to the non-air part have a same activity concentration distribution.

13. The apparatus according to claim 9, wherein, when determining the residual true coincidence count ratio for each of the multiple beds of the PET scan according to the initial PET data, the attenuation correction factor, and the scattering correction factor for the bed, the machine-executable instructions cause the processor to:

determine the residual true coincidence count ratio for each of the multiple beds of the PET scan by performing a calculation with the following formula:

$$\lambda=(E-S)/(A*E),$$

wherein E denotes the initial PET data of one of the multiple beds of the PET scan, S denotes the scattering correction factor of the bed, A denotes the attenuation correction factor of the bed, and λ denotes the residual true coincidence count ratio of the bed.

14. The apparatus according to claim 9, wherein, when determining the scanning time proportion for each of the multiple beds of the PET scan based on the residual true coincidence count ratio for each of the multiple beds of the PET scan, the machine-executable instructions cause the processor to:

calculate a reciprocal for each of the residual true coincidence count ratios; and set the scanning time proportion for each of the multiple beds of the PET scan to be equal to the reciprocal of the corresponding residual true coincidence count ratio of the bed.

15. The apparatus according to claim 9, wherein the machine-executable instructions further cause the processor to:

determine a scattering impact factor for each of the multiple beds of the PET scan according to the initial PET data and the scattering correction factor of the bed; and adjust the scanning time proportion for each of the multiple beds of the PET scan with the scattering impact factor of each of the multiple beds of the PET scan.

16. The apparatus according to claim 15, wherein, when adjusting the scanning time proportion for each of the beds with the scattering impact factor of each of the multiple beds of the PET scan, the machine-executable instructions cause the processor to:

calculate the scanning time proportion for each of the multiple beds of the PET scan with the following formula:

$$\tau=1/\lambda+\alpha*S/(E-S),$$

wherein E denotes the initial PET data of one of the multiple beds,

S denotes the scattering correction factor of the bed, $\alpha$ denotes an empirical constant, $\lambda$ denotes the residual true coincidence count ratio of the bed, and $\tau$ denotes the scanning time proportion of the bed.

* * * * *